US00PP23130P2

(12) United States Plant Patent
Oostveen

(10) Patent No.: US PP23,130 P2
(45) Date of Patent: Oct. 23, 2012

(54) ***HIBISCUS* PLANT NAMED 'EXTREPINK'**

(50) Latin Name: *Hibiscus moscheutos*
Varietal Denomination: Extrepink

(75) Inventor: Cornelis A. Oostveen, De Kwakel (NL)

(73) Assignee: De Zonnebloem Breeding B.V., De Kwakel (NL)

( * ) Notice: Subject to any disclaimer, the term of this patent is extended or adjusted under 35 U.S.C. 154(b) by 95 days.

(21) Appl. No.: 12/928,265

(22) Filed: Dec. 7, 2010

(51) Int. Cl.
*A01H 5/00* (2006.01)

(52) U.S. Cl. ..... Plt./257

(58) Field of Classification Search ..... Plt./257
See application file for complete search history.

*Primary Examiner* — June Hwu

(74) *Attorney, Agent, or Firm* — C. A. Whealy

(57) ABSTRACT

A new and distinct cultivar of *Hibiscus* plant named 'Extrepink', characterized by its upright and somewhat outwardly spreading plant form; dark green-colored leaves; freely flowering habit; large light red purple-colored flowers with darker red purple-colored centers and venation; and good flower longevity.

2 Drawing Sheets

Botanical designation: *Hibiscus moscheutos*.
Cultivar denomination: 'EXTREPINK'.

BACKGROUND OF THE INVENTION

The present invention relates to a new and distinct cultivar of *Hibiscus* plant, botanically known as *Hibiscus moscheutos* and hereinafter referred to by the name 'Extrepink'.

The new *Hibiscus* plant is a product of a planned breeding program conducted by the Inventor in De Kwakel, The Netherlands. The objective of the breeding program is to create new compact *Hibiscus* plants with attractive and large flowers.

The new *Hibiscus* plant originated from a cross-pollination in August, 2008 in De Kwakel, The Netherlands of *Hibiscus moscheutos* 'Sparkle', disclosed in U.S. Plant Pat. No. 21,798 as the female, or seed, parent with a proprietary selection of *Hibiscus moscheutos* identified as code number CB51, not patented, as the male, or pollen, parent. The new *Hibiscus* plant was discovered and selected by the Inventor as a single flowering plant from within the progeny of the stated cross-pollination in a controlled greenhouse environment in De Kwakel, The Netherlands in July, 2009.

Asexual reproduction of the new *Hibiscus* plant by vegetative cuttings in a controlled greenhouse environment in De Kwakel, The Netherlands since August, 2009, has shown that the unique features of this new *Hibiscus* plant are stable and reproduced true to type in successive generations.

SUMMARY OF THE INVENTION

Plants of the new *Hibiscus* have not been observed under all possible environmental conditions. The phenotype may vary somewhat with variations in environment conditions such as temperature and light intensity without, however, any variance in genotype.

The following traits have been repeatedly observed and are determined to be the unique characteristics of 'Extrepink'. These characteristics in combination distinguish 'Extrepink' as a new and distinct *Hibiscus* plant:

1. Upright and somewhat outwardly spreading plant form.
2. Dark green-colored leaves.

3. Freely flowering habit.
4. Large light red purple-colored flowers with darker red purple-colored centers and venation.
5. Good flower longevity.

Plants of the new *Hibiscus* can be compared to plants of the parent, 'Sparkle'. Plants of the new *Hibiscus* differ primarily from plants of 'Sparkle' in flower color as plants of 'Sparkle' have white-colored flowers with red purple-colored centers and venation.

Plants of the new *Hibiscus* can be compared to plants of the male parent selection. Plants of the new *Hibiscus* differ primarily from plants of the male parent selection in the following characteristics:

1. Plants of the new *Hibiscus* are more compact than and not as vigorous as plants of the male parent selection.
2. Plants of the new *Hibiscus* have narrower leaves than plants of the male parent selection.
3. Plants of the new *Hibiscus* and the male parent selection differ in flower color as plants of the male parent selection have purple-colored flowers.

Plants of the new *Hibiscus* can be compared to plants of *Hibiscus moscheutos* 'Mauvelous', not patented. Plants of the new *Hibiscus* differ primarily from plants of 'Mauvelous' in the following characteristics:

1. Plants of the new *Hibiscus* are not as compact as plants of 'Mauvelous'.
2. Flowers of plants of the new *Hibiscus* and 'Mauvelous' differ in color as plants of 'Mauvelous' have darker-colored flowers.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of typical flowering plants of 'Extrepink' grown in a container.

The photograph at the top of the second sheet is a close-up view of a typical flower of 'Extrepink'.

The photograph at the bottom of the second sheet is a close-up view of a typical leaf of 'Extrepink'.

DETAILED BOTANICAL DESCRIPTION

The aforementioned photographs and following observations, measurements and values describe plants grown during the late summer in five-liter containers in a glass-covered greenhouse in De Kwakel, The Netherlands and under conditions which closely approximate commercial *Hibiscus* production. During the production of the plants, day temperatures ranged from 18° C. to 33° C. and night temperatures ranged from 15° C. to 25° C. Plants were 14 weeks old when the photographs and the description were taken. In the description, color references are made to The Royal Horticultural Society Colour Chart, 2007 Edition, except where general terms of ordinary dictionary significance are used.

Botanical classification: *Hibiscus moscheutos* 'Extrepink'.

Parentage:

*Female, or seed, parent.*—*Hibiscus moscheutos* 'Sparkle', disclosed in U.S. Plant Pat. No. 21,798.

*Male or pollen parent.*—Proprietary selection of *Hibiscus moscheutos* identified as code number CB51, not patented.

Propagation:

*Type.*—By vegetative cuttings.

*Time to initiate roots, summer.*—About seven days at temperatures of 22° C.

*Time to initiate roots, winter.*—About ten days at temperatures of 19° C.

*Time to produce a rooted young plant, summer.*—About three weeks at temperatures of 21° C.

*Time to produce a rooted young plant, winter.*—About four weeks at temperatures of 18° C.

*Root description.*—Medium in thickness, fibrous; white to light brown in color.

*Rooting habit.*—Freely branching; dense.

Plant description:

*Plant form and growth habit.*—Upright and somewhat outwardly spreading plant form, broad inverted triangular plant form; moderately vigorous growth habit.

*Branching habit.*—Moderate branching habit, usually about eight lateral branches develop; pinching enhances lateral branch development.

*Plant height.*—About 65.9 cm.

*Plant diameter* (*area of spread*).—About 69.3 cm.

Lateral branch description:

*Length.*—About 49.6 cm.

*Diameter.*—About 6 mm.

*Internode length.*—About 3.2 cm.

*Strength.*—Moderately strong.

*Texture.*—Smooth, glabrous.

*Color.*—Close to 143B.

Foliage description:

*Arrangement.*—Alternate, simple.

*Length.*—About 11.1 cm.

*Width.*—About 7.5 cm.

*Shape.*—Ovate.

*Apex.*—Apiculate.

*Base.*—Cordate.

*Margin.*—Crenate to serrate.

*Texture, upper surface.*—Smooth, glabrous.

*Texture, lower surface.*—Pubescence along midvein.

*Venation pattern.*—Pinnate.

*Color.*—Developing leaves, upper surface: Close to 143A. Developing leaves, lower surface: Close to 138B. Fully expanded leaves, upper surface: Darker than N137D and 147A; venation, close to 144D. Fully expanded leaves, lower surface: Close to 147B; venation, close to 144D.

*Petiole.*—Length: About 6.8 cm. Diameter: About 3 mm. Texture, upper and lower surfaces: Smooth, glabrous. Color, upper and lower surfaces: Close to 144A to 144B.

Flower description:

*Flower arrangement.*—Large rotate flowers arranged singly at terminal leaf axils; freely flowering habit with about 24 flowers developing per plant; flowers face mostly outwardly to slightly upright.

*Fragrance.*—None detected.

*Flower longevity.*—Good flower longevity, flowers last for about four days; flowers not persistent.

*Natural flowering season.*—Plants flower from late summer into the autumn in The Netherlands; plants begin flowering about ten weeks after planting.

*Flower diameter.*—About 18.1 cm.

*Flower length* (*height*).—About 5.8 cm.

*Flower bud.*—Rate of opening: Flowers buds open in about four days. Length: About 4.3 cm. Diameter: About 3.2 cm. Shape: Ovate. Color: Close to 143C and 144A; towards the apex, close to 58A and 59C.

*Petals.*—Arrangement: Corolla consists of five petals in a single whorl; petals imbricate. Length: About 9.4 cm. Width: About 10.6 cm. Shape: Broadly obovate to broadly flabellate. Apex: Rounded and cuspidate. Base: Attenuate. Margin: Entire. Texture, upper and lower surfaces: Smooth, glabrous. Color: When opening, upper surface: Close to 73B; towards the apex, close to 68B; at the base, close to 61B; venation, close to 61C. When opening, lower surface: Close to 68B; towards the apex, close to 68A. Fully opened, upper surface: Close to 73B; towards the apex, close to 68B; at the base, close to 61C; venation, close to 61D; main color becoming closer to 73B with development. Fully opened, lower surface: Close to 68B; towards the apex, close to 68A.

*Sepals.*—Appearance: Five sepals fused into a tubular star-shaped calyx. Length: About 4.4 cm. Width: About 2.4 cm. Shape: Ovate. Apex: Abruptly acute. Margin: Entire. Texture, upper and lower surfaces: Pubescent. Color, immature, upper surface: Close to 144A to 144B. Color, immature, lower surface: Close to 143C and 144A. Color, mature, upper surface: Close to 143C and 143D. Color, mature, lower surface: Close to 143B.

*Peduncles.*—Length: About 8.5 cm. Diameter: About 2.5 mm Angle: About 30° from the lateral branch axis. Strength: Moderately strong. Texture: Smooth, glabrous. Color: Close to 143C.

*Reproductive organs.*—Androecium: Stamen number: Numerous, about 150. Filament length: About 4 mm. Filament color: Close to N155B to N155C. Anther shape: Orbicular. Anther length: About 2 mm. Anther color: Close to 5D. Amount of pollen: Moderate. Pollen color: Close to 8B. Gynoecium: Pistil length:

About 4.1 cm. Style length: About 3.9 cm. Style color: Close to N155C. Stigma appearance: Five-parted, club-shaped. Stigma color: Close to 48A to 48B. Ovary color: Close to 65A.

*Seeds/fruits*.—Seed and fruit development have not been observed.

Temperature tolerance: Plants of the new *Hibiscus* have been observed to tolerate high temperatures of about 35° C. and to be hardy to USDA Hardiness Zone 6.

Pathogen/pest resistance: Plants of the new *Hibiscus* have not been observed to be resistant to pathogens and pests common to *Hibiscus*.

It is claimed:

1. A new and distinct *Hibiscus* plant named 'Extrepink' as illustrated and described.

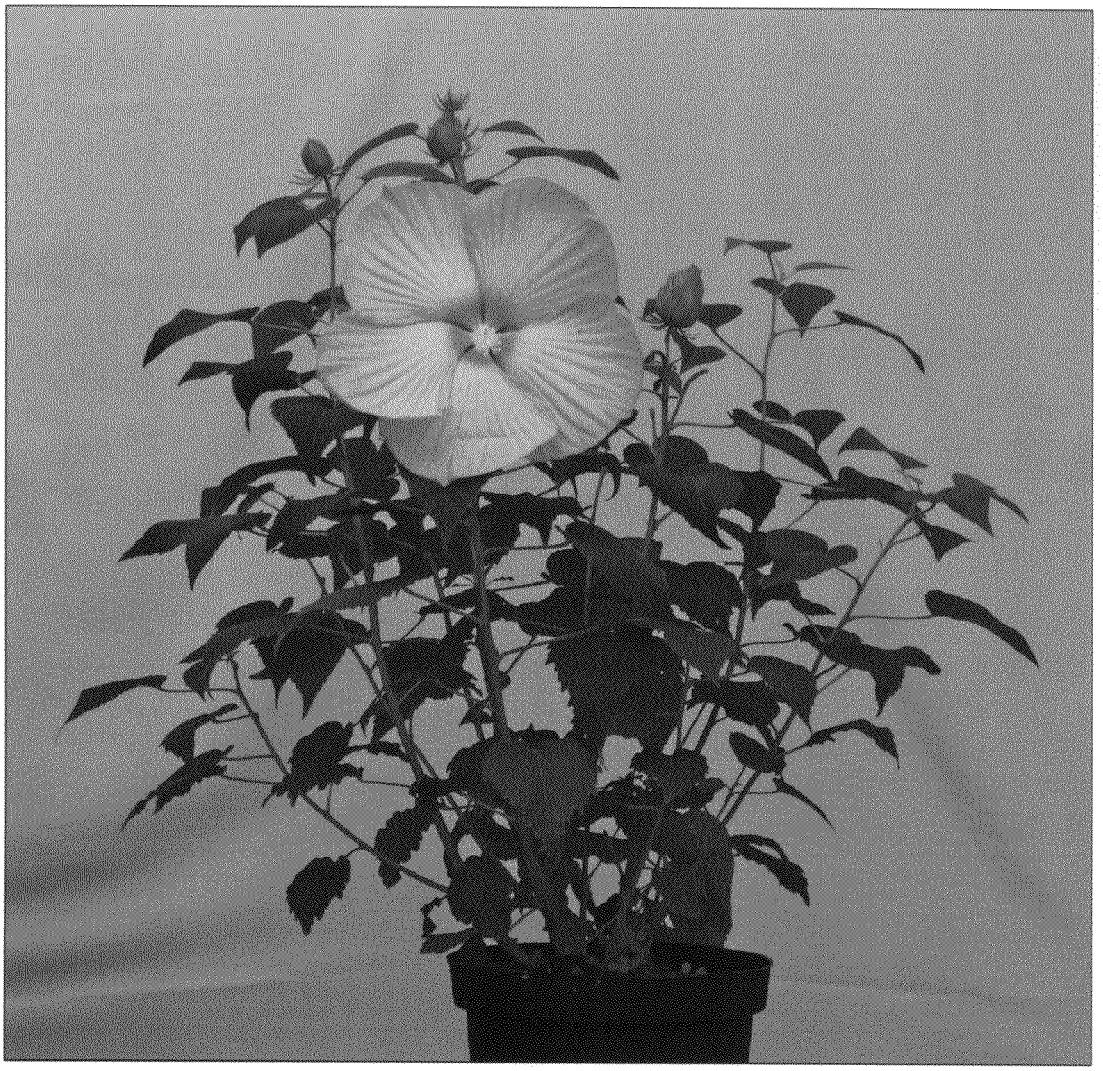

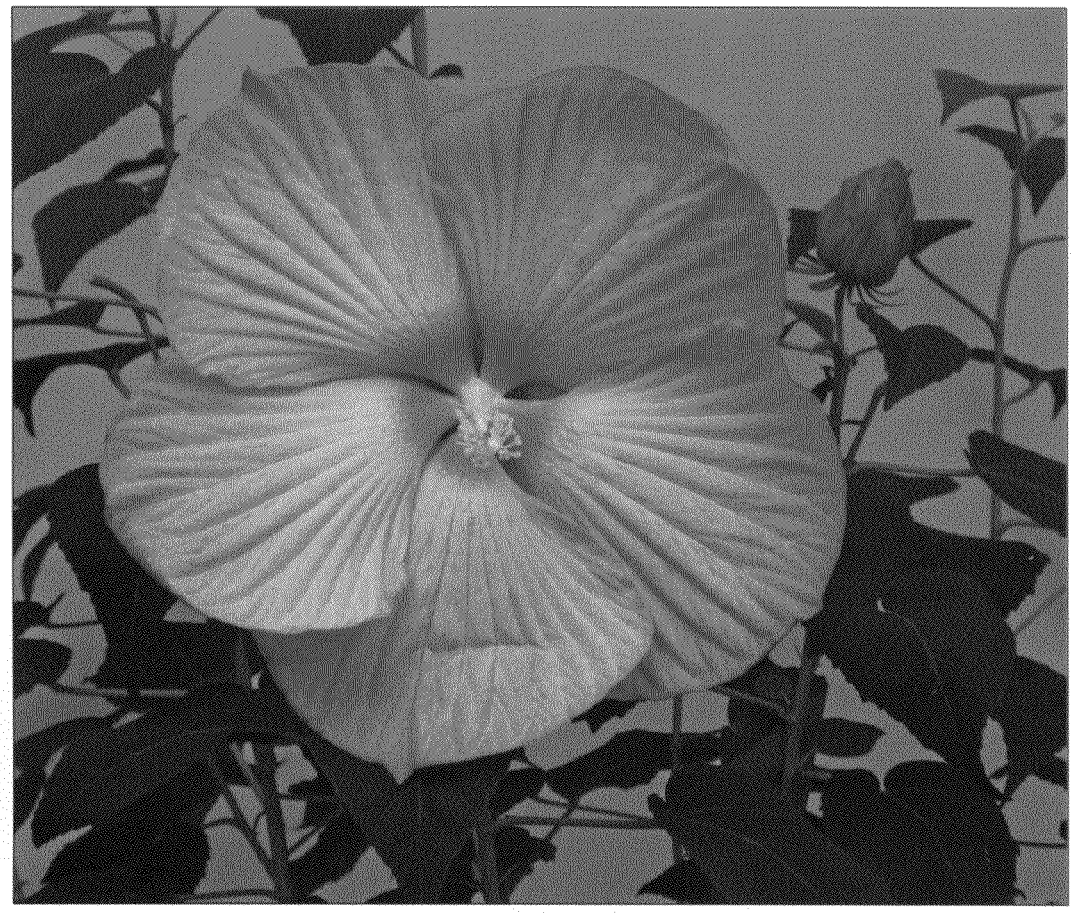
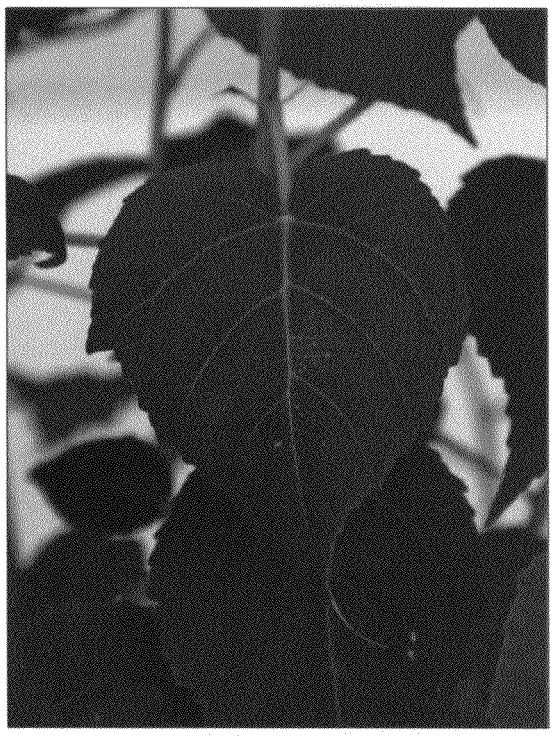

* * * * *